United States Patent [19]
Collins et al.

[11] Patent Number: 5,780,018
[45] Date of Patent: Jul. 14, 1998

[54] COSMETIC FORMULATIONS

[75] Inventors: Rosemary Collins; Sandra Cox, both of Nottinghamshire, United Kingdom

[73] Assignee: The Boots Company PLC, Notts, United Kingdom

[21] Appl. No.: 475,347

[22] Filed: Jun. 7, 1995

Related U.S. Application Data

[62] Division of Ser. No. 150,191, Dec. 8, 1993, abandoned.

[30] Foreign Application Priority Data

| Jun. 21, 1991 | [GB] | United Kingdom | 9113481 |
| Jun. 21, 1991 | [GB] | United Kingdom | 9113482 |

[51] Int. Cl.$^6$ ............................... A61K 7/027
[52] U.S. Cl. ............... 424/64; 424/63; 424/498; 424/DIG. 5
[58] Field of Search ............... 424/63, 64, 498, 424/DIG. 5

[56] References Cited

U.S. PATENT DOCUMENTS 5,225,186 7/1993 Castrogiovanni et al. ............... 424/64

FOREIGN PATENT DOCUMENTS

| 36199 | 9/1981 | European Pat. Off. |
| 47573 | 3/1982 | European Pat. Off. |
| 147905 | 7/1985 | European Pat. Off. |
| 57903 | 8/1970 | Luxembourg |
| 9106277 | 5/1991 | WIPO |

OTHER PUBLICATIONS

Klinglake V., Lipstick Formulation and Production: Something of an Art. *Soap, Perfumery and Cosmetics*, vol. 54, No. 7, pp. 359–363, 1981.

*Primary Examiner*—Jyothsan Venkat
*Attorney, Agent, or Firm*—Nikaido Marmelstein Murray & Oram LLP

[57] ABSTRACT

A novel process for the manufacture of a lipstick is described which comprises melting a combination of colour pellets together with a measured amount of an oil blend with mixing to give a lipstick base composition and moulding said base composition into a lipstick of a predetermined colour. A colour pellet comprises: 1–50% by weight of a wax component; b) 30–65% by weight of an oil component; and c) 10–35% by weight of a pigment and/or a pearlising agent.

A kit of parts suitable for implementing the process is described. The process is particularly suitable for the clean and efficient manufacture of lipsticks, of a wide range of colour, at the point of sale.

10 Claims, 2 Drawing Sheets

COSMETIC FORMULATIONS

This is a division of application Ser. No. 08/150,191 filed Dec. 8, 1993 now abandoned.

This invention relates to a novel process for the manufacture of lipsticks and to novel intermediates used in said process.

A lipstick should possess certain physical properties to be acceptable to a consumer. It should, for example have a suitable texture to permit smooth and rapid application with the minimum of pressure. The applied film should be resistant to the mild abrasion encountered during eating, drinking, or smoking. In addition the composition of the lipstick should be such that the colour is retained only on that portion of the lip to which it is applied so that the colour does not spread onto the skin adjacent to the lips. It is also important that the perfume selected has an acceptable taste.

Once these physical characteristics have been obtained then the choice of colour is a very important consideration for the consumer when purchasing a lipstick. At any moment in time the colours in most popular demand are dictated by the highly volatile world of fashion, and this may result in rapid changes in demand. These rapid changes in demand have undesirable consequences. Firstly, the consumer may find it impossible to obtain her own favourite colour of lipstick as the overall demand for that colour has fallen and the line has been discontinued. Secondly, the retailers may find that, due to a reduction in demand for a particular shade or colour, they are left with excess stock for which there is no market. Thirdly, the retailers may not have a new colour in stock as they have been unable to respond quickly enough to the new trend in fashion.

The need to offer the customer a wide choice of colours of lipstick may cause problems in stock control for the retailer. Either a comparatively large area must be set aside to maintain a stock of a wide variety of colours and shades, with the concomitant risk of excess stock, or else a very efficient stock control and ordering system must be maintained.

In an effort to solve some of these problems an attempt has been made to blend lipstick at the point of sale. Dispersions of pigments in oils were used which were mixed with a base composition to give a desired colour or shade. There were many unresolved problems with this system, however. Firstly, it was difficult to maintain stable, homogeneous dispersions of the pigment in the oils. This led to a loss of accuracy in the formulation, resulting in colour and shade variation which was not acceptable to the consumer. Secondly, the equipment necessary to blend the final product into a satisfactory form (for example a high shear mixer) was not suitable for use at the point of sale. Thirdly, the difficulties involved in measuring, transferring and mixing liquids made it difficult to achieve a rapid, clean and efficient process.

The applicants have now found a novel process for the manufacture of lipstick which may optionally be used at the point of sale. This process increases the choice of colour available to the consumer, decreases losses incurred by the retailer due to surplus stock, reduces stock control problems and does not suffer from the disadvantages of the previous point of sale formulation process. The present invention provides a process for the manufacture of a lipstick comprising a) melting a combination of colour pellets together with a measured amount of an oil blend with mixing to give a homogeneous lipstick base composition and b) moulding said base composition into a lipstick of a predetermined colour.

Suitably the colour pellets may be melted by any of the methods known in the art for melting wax/oil mixtures. Preferably the melting process is carried out by means of a heating block, a steam bath, a water bath, a conventional oven, a microwave oven, a flame or a hot air blower. More preferably the melting process is carried out by means of a heating block or a microwave oven. Suitably the colour pellets are melted at a temperature in the range 40°–120° C. Preferably the colour pellets are melted at a temperature in the range 60°–100° C. more preferably 70°–90° C. and most preferably in the range 75–85° C.

Suitably mixing may be carried out by any method known to those skilled in the art for mixing liquids and suspended solids for example manual, mechanical, electrical or magnetic, stirring or shaking. Preferably the combination of colour pellets and the oil blend is stirred manually.

Suitably the base composition may be moulded by pouring the warm base composition into a mould of the desired shape. Suitably the lipstick may be moulded into a standard "bullet" shape for example using a single or multiple cavity split mould or hot filled directly into a godet or compact in one of a variety of shapes and from which the lip product may be applied using a brush. Optionally the lipstick may be moulded directly into a suitably adapted lipstick case. Optionally the moulded lipstick is cooled for example using a cool box on a refrigerator.

The colour pellets used in the present invention are believed to be novel. The present invention provides a colour pellet comprising a) 1–50% by weight of a wax component, b) 30–65% by weight of an oil component, and c) 10–35% by weight of a pigment and/or pearlising agent. Colour pellets may optionally further comprise one or more conventional lipstick ingredients such as for example gloss modifiers, texture modifiers, moisturising agents, soothing agents, conditioners, vitamins, sunscreens, preservatives and antioxidants. It will be understood by a person skilled in the art that all the above ingredients must be cosmetically acceptable.

Suitably the wax component comprises one or more cosmetically acceptable waxes for example a plant or vegetable wax (for example carnauba wax and candelilla wax), a paraffin wax (for example ozokerite), an animal wax (for example beeswax or lanolin) or a synthetic wax (for example hydrogenated castor oil) . Preferably the wax component may comprise 10–40% by weight of the colour pellet, more preferably 15–35% and in an especially preferred embodiment the wax component comprises 20–30% of the colour pellet.

Suitably the oil component of the colour pellet comprises one or more cosmetically acceptable oils and/or one or more cosmetically acceptable fats. Suitable oils comprise natural oils (e.g. castor oil, lanolin oil, almond oil and wheat-germ oil), synthetic esters (e.g. pentaerythritol tetracaprylate and pentaerythritol tetracaprate) , fatty oils (for example triglyceride esters), and fatty alcohols (e.g. oleyl alcohol and octyldodecanol). Suitable fats comprise animal fats (for example wool fat), vegetable fats (for example triglyceride esters) and mineral fats (for example white soft paraffin). Preferably the oil component may comprise 35–60% by weight of the colour pellet, more preferably 40–55% and most preferably 50–55% for example 52–54%.

The pigment may be a single pigment or a mixture of pigments. Suitably any conventional lipstick pigment or cosmetically acceptable pearlising agent may be used. Preferred pigments include for example iron oxides, titanium dioxide, lakes, ultramarines and organic-dyes. Preferred pearlising agents are titanium dioxide coated mica, pigmented mica, pigmented titanium dioxide coated mica and bismuth oxychloride. The pigment and the pearlising agent together comprise preferably 15-30% by weight of the colour pellet and more preferably 20-25%. Most preferably the pigment and the pearlising agent together comprise 22-24% of the colour pellet.

Optionally the colour pellet further comprises a preservative and/or an antioxidant and/or a perfume. Any conventional lipstick preservative, anti-oxidant and perfume may be employed. A preferred preservative is propyl-p-hydroxybenzoate. A preferred anti-oxidant is butylated hydroxyanisole.

The colour pellets may be combined with an oil blend, as described earlier, to form a lipstick. Suitably, the oil blend comprises one or more cosmetically acceptable oils for example natural oils (e.g. castor oil, lanolin oil, almond oil and wheat-germ oil), synthetic esters (e.g. pentaerythritol tetracaprylate and pentaerythritol tetracaprate), fatty oils (for example triglyceride esters) and fatty alcohols (e.g. oleyl alcohol and octyldodecanol) or a mixture thereof. Optionally the oil blend may further comprise an animal fat, a vegetable fat or a mineral fat. Optionally the oil blend may further comprise a soothing agent, for example a plant extract (e.g. comfrey extract and sunflower seed oil), a moisturising agent (for example wheat-germ oil or an alkylene glycol e.g. butylene glycol), a preservative (e.g. propyl-p-hydroxybenzoate) an anti-oxidant (e.g. butylated hydroxyanisole) and a perfume.

The present invention offers numerous advantages. A very extensive range of colours and shades is made available to the consumer while at the same time alleviating the stock control problems of the retailer. The colour pellets may be formulated in the factory with a high degree of accuracy and homogeneous colour dispersion which leads to reliable reproducibility in the colour of the lipstick obtained.

It will be appreciated that the shape of the colour pellets is not important. The term pellet is used herein to describe a colour unit of a known predetermined weight or volume comprising a wax component, an oil component and a predetermined amount of pigment and/or pearlising agent. Other optional ingredients may be present as indicated previously. Preferably the pellet is a solid at ambient temperature but a semi-solid paste may also be used provided that a stable, evenly-distributed dispersion of the pigment and/or pearlising agent is obtained in bulk manufacture which may be divided into a number of identical colour units. Preferably the colour pellet is of known weight. Suitably the weight of the pellet lies in the range 0.1-10 g. Preferably the weight is in the range 0.2-5.0 g and more preferably lies in the range 0.5-1.5 g.

Since the shape of the colour pellet is not important any method known to those skilled in the art for the division of a molten bulk mixture into a number of identical units of a solid or semi-solid state may be employed to prepare the colour pellets. Suitably the bulk mixture may be hoe filled into a suitable receptacle (for example a mould or a blister tray) optionally using a metered dose system. Alternatively the bulk mixture may be extruded and then cut to provide the pellets or the bulk mixture may be pastillised. Preferably the colour pellets are prepared using a metered dose system.

The colour pellets are easy to store and to handle. They may be dispensed, quickly and accurately, directly into the container in which the lipstick base composition is to be mixed. The process for producing the lipstick is simple, rapid and efficient. Gravimetric measurements of ingredients are not required. The operator has only to count out the different colour pellets to be added according to a predetermined formula and then add the required number of doses of the oil blend as dictated by the same formula.

In another aspect the present invention provides a kit of parts for the formulation of a range of lipsticks of similar base composition but of different colour, comprising a master-list, a range of colour pellets, an oil dispenser adapted to dispense a known dose of an oil blend, a mixing vessel, melting means, mixing means and moulding means wherein said master-list comprises a composition for each colour of lipstick in the range and indicates the number of each colour pellet to be added and further indicates the number of doses of the oil blend to be added to produce, after melting, mixing and moulding, a lipstick of each colour in the range. Optionally the kit further comprises cooling means to cool the moulded lipstick. Preferably for each range of lipsticks the total number of colour pellets and doses of oil blend is the same for each individual lipstick but the colours of the colour pellets are varied to produce each predetermined colour in the range.

In yet another aspect the present invention provides a refill pack for the above mentioned kit comprising a plurality of colour pellets and doses of oil blend. Optionally disposable mixing vessels may be included in the refill kit.

The invention will now be illustrated by the following specific description which is given by way of example.

The colour pellets are formed by the following process. It will be understood that the composition for each pellet is multiplied up according to the number of pellets to be made to provide a colour pellet bulk mix. The wax component is melted, with stirring at 70°-80° C. and the remaining portion of the oil component added. The pigment and a further portion of the oil component are mixed together, for example using a mill e.g. a triple roller mill, to form a colour paste. The colour paste, or pastes where more than one pigment is used, is added to the warm mixture of the wax component and the portion of the oil component. This mixture is thoroughly homogenised using a high shear mixer and then the pearlising agent and the preservatives are added with stirring. The mixture is then poured into a scraping jig, for example as illustrated in FIGS. 1 and 2, or into a metered dose filling system as illustrated in FIG. 3. In the accompanying drawings:

Figure 1:
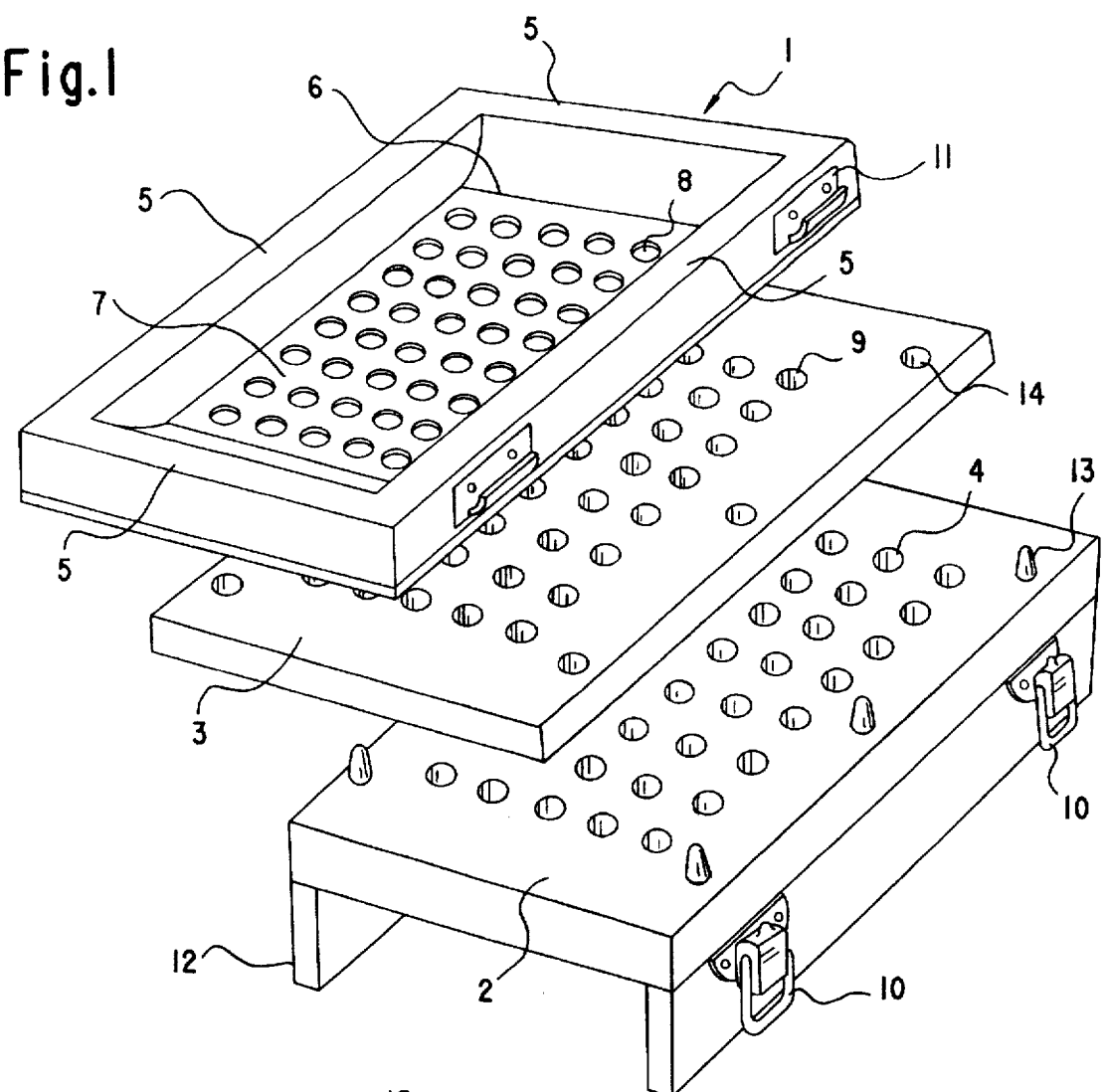
FIG. 1 is a diagrammatic exploded view of a scraping jig.
Figure 2:
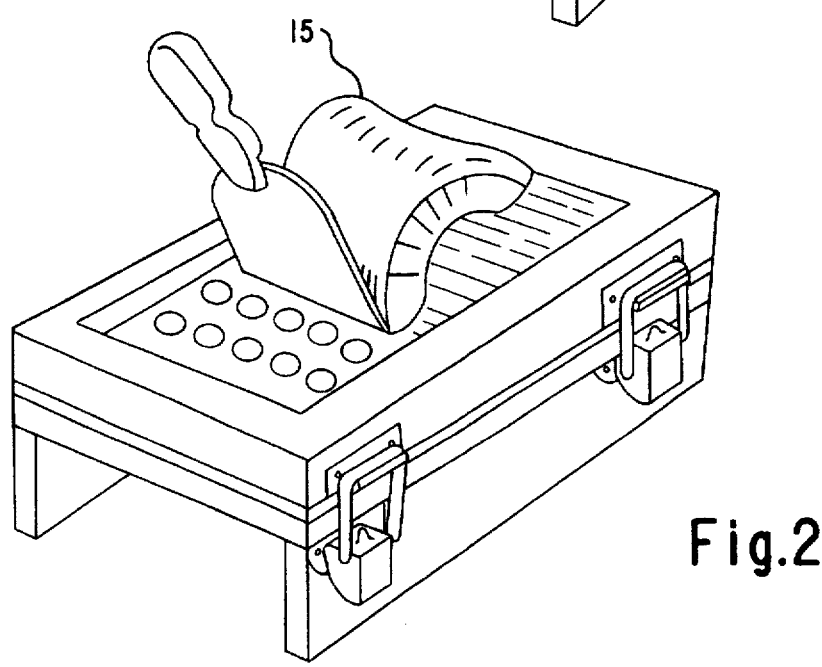
FIG. 2 is a diagrammatic view of the scraping jig in operation

The illustrative scraping jig comprises a filling head (1) and a base plate (2) with indentations (4) wherein said base-plate (2) is adapted to support a blister tray (3). The blister tray is of the type used conventionally used to store pharmaceutical tablets. The filling head comprises four walls (5) defining a filling reservoir (6) and a perforated bottom plate (7) adapted such that each perforation (8) coincides with an opening to a blister (9) in the blister tray (3). The filling head is adapted to co-operate with said base-plate (2) by fastening means (10) and (11) to form a sealed unit. The scraping jig comprises a stand (12) to support said base-plate and locating pegs (13) on the base-plate adapted to co-operate with locating apertures (14) on the blister tray and with locating holes (not shown) in the filling head. Thus the perforations (8) in the filling head are aligned with the openings to the blisters (9) and the blisters are received in the indentations (4) in the base plate. In operation a blister tray (3), which has ben sprayed with a silicone release agent, is placed into the base-plate and then the filling head and the base-plate are fastened together. The molten colour pellet bulk mix is poured into the filling head at a suitable rate to avoid entrapment of air in the blisters as they are filled by the bulk mix passing through the perforations. On cooling, excess material (15) is scraped off using a scraper as illustrated in FIG. 2. Two opposite walls of the reservoir are chamfered to facilitate the removal of excess material as shown in FIG. 1. The blister pack is removed and a conventional blister tray cover applied to enclose the blisters and form a blister pack.

Figure 3:
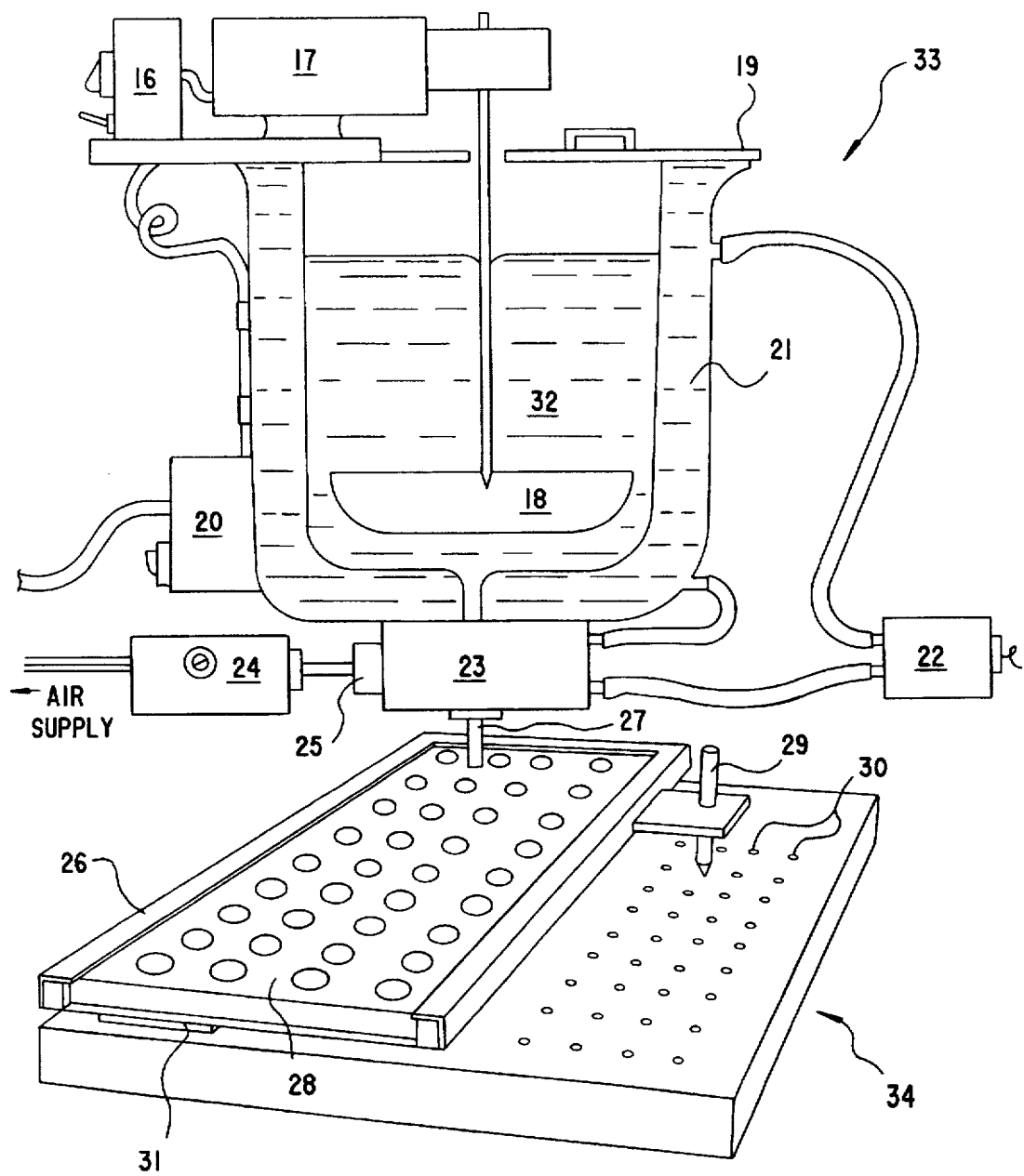
FIG. 3 is a diagrammatic view of a metered dose filling system.

The illustrative metered dose filling system (FIG. 3) comprises a metered dose dispenser (33) and a blister tray housing (26), movable by means of slides (31) (not all shown) with respect to a base plate (34), adapted to receive a blister tray (28). The metered dose dispenser (33) comprises a liquid reservoir (32) with an inlet, adapted to receive a stirrer (18) through a removable lid (19), and an outlet controlled by an outlet valve (not shown) leading to a piston chamber (23) from which liquid is dispensed through a valve-controlled nozzle (27) into the blister tray (28) by means of a piston (25) operated by an air-driven piston motor drive (24) which has a stroke adjuster. The dispenser further comprises a heating jacket (21) for the reservoir wherein the temperature is controlled by means of a thermostatically controlled heater (20) and water is circulated through the jacket and the piston chamber (23) by a water pump (22). Typically, the filling mixture is maintained at a temperature in the range 70°–80° C. In the illustrative example in FIG. 3 the stirrer (18) is powered by a motor (17) and regulated by a control box (16).

In operation the molten filling mixture is poured into the reservoir where it is stirred and heated. On the fill stroke of the piston the outlet valve of the reservoir opens, the nozzle valve closes and the filling mixture is drawn into the piston chamber. On the emptying stroke of the piston the outlet valve closes, the nozzle valve opens and the filling mixture passes through the open valve leading to the nozzle (27) from which it is dispensed into a blister of the blister tray. The blister tray housing is then moved manually by means of the locating device (29) and positioned using the locating indentations (30) until the desired number of blisters contain the desired amount of material. The blister tray is removed and sealed in a conventional manner to form a blister pack.

Suitable metered dose dispensers are supplied by Kemwall Ltd. preferred model is the "10 Litre Dispensing Vessel". It will be appreciated by those skilled in the art that many modifications may be made to the above metered dose dispenser all of which will perform the function satisfactorily. For example, alternative methods of a) driving the stirrer; b) heating the jacket; c) driving the piston and d) moving the blister housing may be employed. Alternatively the dispenser may be movable with respect to the blister housing.

These blister packs containing the colour pellets are then sent to the point of sale where they may be formulated into lipsticks. By combination of the colour pellets described in the Examples, hereinafter, a range, of for example, 240 different shades of lipstick may initially be obtained. These shades will be displayed as tester lipsticks for customers to apply to their skin. Customers may choose to combine any two of these shades thus giving a choice of over 28,000 shades.

Once a particular shade has been selected by the customer then the operating assistant consults a reference chart to ascertain the number and type of colour pellets required to produce this shade. Those pellets are pressed out of the blister packs into a suitable container, for example a plastic beaker, and the lipstick prepared as follows.

Typically a measured dose of the oil blend is 25 dispensed from a pump dispenser into the container containing the predetermined number of colour pellets. The mixture is melted in a microwave oven. The molten mixture is removed from the oven and stirred with a spatula bug, hand until homogeneous. The mixture is then returned to the microwave oven and reheated to 80°–85° C. The mixture is then poured into a single cavity split mould. On cooling, the lipstick is removed from the mould and after insertion into a suitable case is dispensed to the customer.

In the following Examples the materials used were supplied under the Tradenames shown below by the suppliers listed.

| MATERIAL | TRADENAME | SUPPLIER |
| --- | --- | --- |
| OZOKERITE | WHITE OZOKERITE 8289 | POTH HILLE |
|  | WHITE OZOKERITE 7488 | POTH HILLE |
|  | WHITE OZOKERITE 7726 | POTH HILLE |
| MICROCRYSTALLINE WAX | MULTIWAX X145 AH | WITCO |
|  | OKERIN WAX 239 | ASTOR CHEMICALS LTD |
|  | OKERIN WAX 4386M | ASTOR CHEMICALS LTD |
| CAPRYLIC/CAPRIC/ | SOFTISAN 645 | DYNAMIT NOBEL |
| ISOSTEARIC/ADIPIC/ | SOFTISAN 649 |  |
| TRIGLYCERIDES MIXTURE |  |  |
| POLYGLYCEROL POLYESTER | CITHROL PR | CRODA CHEMICALS LTD |
| MIXTURE OF NATURALLY |  |  |
| OCCURRING FATTY ACIDS |  |  |
| OCTYLDODECANOL | EUTANOL G | HENKEL |
| CASTOR OIL | CASTOR OIL BP PHARM |  |
| OLEYL ALCOHOL | NOVOL | CRODA CHEMICALS LTD |
| LANOLIN OIL | LANTROL | CRODA CHEMICALS LTD |
| PENTAERYTHRITOL | CRODAMOL PTC | CRODA CHEMICALS LTD |
| TETRACAPRYLATE/CAPRATE |  |  |
| COMFREY EXTRACT (AND) | HERBAL EXTRACT COMFREY | ALBAN MULLER |
| SUNFLOWER SEED OIL |  | INTERNATIONAL |
| TITANIUM DIOXIDE COATED | TIMIRON STARLUSTER MP 115 | RONA |
| MICA (1) |  |  |
| TITANIUM DIOXIDE COATED | TIMIRON SUPERSHEEN MP 1001 | RONA |
| MICA (2) |  |  |
| D&C RED NO. 27 ALUMINIUM | PINK 1898 ANST | D F ANSTEAD |
| LAKE |  |  |

-continued

| MATERIAL | TRADENAME | SUPPLIER |
|---|---|---|
| D&C RED NO. 6 BARIUM LAKE | TUDOR ORCHID A506.10 | KINGFISHER COLOURS |
| IRON OXIDES (3) | TUDOR EBONY A401.02 | KINGFISHER COLOURS |
| IRON OXIDES (4) | TUDOR JUNIPER A411.02 | KINGFISHER COLOURS |
| F.D&C YELLOW NO. 5 ALUMINIUM LAKE | YELLOW NO. 5 FD&C AL LAKE C69-4424 AND C69-002 | SUN CHEMICAL CORP. |
| D&C RED NO. 7 CALCIUM LAKE | RUBINE LAKE C19.011 | SUN CHEMICAL CORP. |
| ULTRAMARINE BLUE | ULTRAMARINE BLUE AR2000 RKT. | RECKITTS COLOURS LTD |

Two ranges of lipstick are described. Firstly, in each range the composition of each pellet is described and then the formation of some lipsticks in the range is described.

The invention is illustrated by the following non-limitative examples. The percentages quoted are by weight of the compositions.

RANGE 1
COLOUR PELLETS

| Example 1 | % W/W |
|---|---|
| HYDROGENATED CASTOR OIL (W) | 3.88 |
| CARNAUBA (W) | 3.97 |
| CANDELILLA WAX (W) | 3.97 |
| OZOKERITE (W) | 8.95 |
| MICROCRYSTALLINE WAX (W) | 2.60 |
| POLYGLYCEROL POLYESTER MIXTURE (O) | 8.61 |
| CASTOR OIL (O) | 32.73 |
| D&C RED NO. 27 ALUMINIUM LAKE (C) | 14.90 |
| OCTYLDODECANOL (O) | 5.81 |
| CAPRYLIC/CAPRIC/ISOSTEARIC/ADIPIC TRIGLYCERIDES MIXTURE (O) | 5.81 |
| ULTRAMARINE BLUE (C) | 3.76 |
| TITANIUM DIOXIDE COATED MICA (2) (PA) | 4.90 |
| BUTYLATED HYDROXYANISOLE (P) | 0.02 |
| PROPYL P-HYDROXYBENZOATE (P) | 0.09 |

The waxes (W) were melted together with stirring at 70°–30° C. A portion of the oils (O) was added at this temperature with stirring followed by the pigments (C) predispersed in the remainder of the oils (O) using a triple roller mill. The mixture was then homogenised using a high shear mixer. The pearlising agent (PA) and the preservatives (P) were added with stirring. The mixture was either poured into the scraping jig illustrated in FIG. 1 or the metered dose filling system illustrated in FIG. 3 to form pellets.

Examples 2 to 14 were prepared in a similar manner to Example 1.

| | % W/W |
|---|---|
| Example 2 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| POLYGLYCEROL POLYESTER MIXTURE | 8.61 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| TITANIUM DIOXIDE COATED MICA (2) | 4.90 |
| IRON OXIDES (3) | 3.61 |
| TITANIUM DIOXIDE | 15.05 |
| BUTYLATED HYDROXYANISOLE | 0.02 |
| PROPYL P-HYDROXYANISOLE | 0.09 |
| Example 3 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| POLYGLYCEROL POLYESTER MIXTURE | 8.61 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| TITANIUM DIOXIDE COATED MICA (1) | 19.95 |
| F, D&C YELLOW NO. 5 ALUMINIUM LAKE | 3.61 |
| BUTYLATED HYDROXYANISOLE | 0.02 |
| PROPYL P-HYDROXYBENZOATE | 0.09 |
| Example 4 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (1) | 19.95 |
| IRON OXIDES (3) | 3.61 |
| BUTYLATED HYDROXYANISOLE | 0.02 |
| PROPYL P-HYDROXYANISOLE | 0.09 |
| Example 5 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| TRIGLYCERIDES MIXTURE | 5.81 |
| POLYGLYCEROL POLYESTER MIXTURE | 8.61 |
| OCTYLDODECANOL | 5.81 |
| D&C RED NO. 7 CALCIUM LAKE | 1.20 |
| TITANIUM DIOXIDE COATED MICA (1) | 22.36 |
| CASTOR OIL | 32.73 |
| BUTYLATED HYDROXYANISOLE | 0.02 |
| PROPYL P-HYDROXYBENZOATE | 0.09 |
| Example 6 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| D&C RED NO. 6 BARIUM LAKE | 1.20 |
| TITANIUM DIOXIDE COATED MICA (1) | 22.36 |

-continued

| | % W/W |
|---|---|
| BUTYLATED HYDROXYANISOLE | 0.02 |
| PROPYL P-HYDROXYBENZOATE | 0.09 |
| Example 7 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| D&C RED NO. 7 CALCIUM LAKE | 3.61 |
| TITANIUM DIOXIDE COATED MICA (1) | 19.95 |
| BUTYLATED HYDROXYANISOLE | 0.02 |
| PROPYL P-HYDROXYBENZOATE | 0.09 |
| Example 8 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| D&C RED NO. 6 BARIUM LAKE | 3.61 |
| TITANIUM DIOXIDE COATED MICA (1) | 19.95 |
| BUTYLATED HYDROXYANISOLE | 0.02 |
| PROPYL P-HYDROXYBENZOATE | 0.09 |
| Example 9 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (2) | 4.90 |
| F, D&C YELLOW NO. 5 ALUMINIUM LAKE | 18.66 |
| BUTYLATED HYDROXYANISOLE | 0.02 |
| PROPYL P-HYDROXYBENZOATE | 0.09 |
| Example 10 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (2) | 4.90 |
| IRON OXIDE (4) | 18.66 |
| BUTYLATED HYDROXYANISOLE | 0.02 |
| PROPYL P-HYDROXYBENZOATE | 0.09 |
| Example 11 | |
| HYDROGENATED CASTOR OIL | 3.88 |
| CARNAUBA | 3.97 |
| CANDELILLA WAX | 3.97 |
| OCTYLDODECANOL | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |

-continued

| | % W/W |
|---|---|
| TITANIUM DIOXIDE COATED MICA (2) | 4.90 |
| D&C RED NO. 7 CALCIUM LAKE | 18.66 |
| BUTYLATED HYDROXYANISOLE | 0.02 |
| PROPYL P-HYDROXYBENZOATE | 0.09 |
| Example 12 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (2) | 4.90 |
| D&C RED NO. 6 BARIUM LAKE | 18.66 |
| BUTYLATED HYDROXYANISOLE | 0.02 |
| PROPYL P-HYDROXYBENZOATE | 0.09 |
| PELLET 13 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (2) | 4.90 |
| TITANIUM DIOXIDE | 18.66 |
| BUTYLATED HYDROXYANISOLE | 0.02 |
| PROPYL P-HYDROXYBENZOATE | 0.09 |
| Example 14 | |
| HYDROGENATED CASTOR OIL | 3.88 |
| CARNAUBA | 3.97 |
| CANDELILLA WAX | 3.97 |
| OZOKERITE | 8.95 |
| MICROCRYSTALLINE WAX | 2.60 |
| CASTOR OIL | 32.73 |
| OCTYLDODECANOL | 5.81 |
| CAPRYLIC/CAPRIC/ISOSTEARIC/ADIPIC TRIGLYCERIDES MIXTURE | 5.81 |
| POLYGLYCEROL POLYESTER MIXTURE | 8.61 |
| TITANIUM DIOXIDE COATED MICA (2) | 23.56 |
| BUTYLATED HYDROXYANISOLE | 0.02 |
| PROPYL P-HYDROXYBENZOATE | 0.09 |
| OIL BLEND 1 | |
| CASTOR OIL | 14.11 |
| PENTAERYTHRITOL TETRACAPRYLATE/CAPRATE | 46.37 |
| OCTYLDODECANOL | 35.44 |
| SWEET ALMOND OIL | 1.30 |
| COMFREY EXTRACT AND SUNFLOWER SEED OIL | 1.30 |
| WHEATGERM OIL | 1.30 |
| PROPYL P-HYDROXYBENZOATE | 0.13 |
| BUTYLATED HYDROXYANISOLE | 0.04 |

The formulation of the colour pellets into lipsticks is described in Examples 15–20. In each example the colour pellets (1.24 g each) and four doses of oil blend (2.4 g each) were mixed and heated to 80°–95° C. in a microwave oven. The mixture was removed and stirred with a spatula until homogeneous. The mixture was reheated to 80°–85° C. and then poured into a single cavity split mould with an overflow channel. The mould was cooled and separated. The lipstick case was inverted over the mould and the lipstick withdrawn into the case. The quantities given above are sufficient for two average size lipsticks allowing for material losses in the process, e.g. by adhesion to the vessel or the thermometer.

Examples of formulae for lipsticks

Example 15 (Fuchsia/Arlethyst) Shade 1

10 of Example 11, 2 of Example 2 and 4 Doses Oil Blend 1.

Example 16 (Claret Mulberry) Shade 41

8 of Example 12, 4 of Example 2, and 4 Doses Oil Blend 1.

Example 17 (Ruby/Pink) Shade 81

4 of Example 13, 2 of Example 11, 6 of Example 12 and 4 Doses Oil Blend 1.

Example 18 (Almond/Spice) Shade 121

6 of Example 2, 4 of Example 12, 2 of Example 10 and 4 Doses Oil Blend 1.

Example 19 (Russet/Sienna) Shade 161

2 of Example 2, 2 of Example 13, 6 of Example 12, 2 of Example 10 and 4 Doses Oil Blend 1.

10 Example 20 (Flame/Coral) Shade 201

10 of Example 12, 2 of Example 13 and 4 Doses Oil Blend 1.

RANGE 2
COLOUR PELLETS

Examples 21–34 below are prepared in a similar manner to Examples 1–14.

|  | % W/W |
|---|---|
| Example 21 | |
| CARNAUBA (W) | 3.63 |
| OZOKERITE (W) | 12.23 |
| MICROCRYSTALLINE WAX (W) | 6.18 |
| LANOLIN (O) | 6.82 |
| D&C RED NO. 27 ALUMINIUM LAKE (C) | 14.90 |
| OLEYL ALCOHOL (O) | 13.44 |
| CASTOR OIL (O) | 34.01 |
| ULTRAMARINE BLUE (C) | 3.76 |
| TITANIUM DIOXIDE COATED MICA (PA) | 4.90 |
| BUTYLATED HYDROXYANISOLE (P) | 0.03 |
| PROPYL-P-HYDROXYBENZOATE (P) | 0.10 |
| Example 22 | |
| CARNAUBA | 3.63 |
| OZOKERITE | 12.23 |
| MICROCRYSTALLINE WAX | 6.18 |
| LANOLIN | 6.82 |
| TITANIUM DIOXIDE COATED MICA (2) | 4.90 |
| IRON OXIDES (3) | 3.61 |
| TITANIUM DIOXIDE | 15.05 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| Example 23 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| F, D&C YELLOW NO. 5 ALUMINIUM LAKE | 3.61 |
| TITANIUM DIOXIDE COATED MICA (1) | 19.95 |
| Example 24 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| IRON OXIDES (3) | 3.61 |
| TITANIUM DIOXIDE COATED MICA (1) | 19.95 |
| Example 25 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE SOLE | 0.03 |
| PROPYL-P-HYDROXYBENZOATE | 0.10 |
| D&C RED NO. 7 CALCIUM LAKE | 1.20 |
| TITANIUM DIOXIDE COATED MICA (1) | 22.36 |
| Example 26 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| D&C RED NO. 6 BARIUM LAKE | 1.20 |
| TITANIUM DIOXIDE COATED MICA (1) | 22.36 |
| Example 27 | |
| CARNAUBA | 3.63 |
| OZOKERITE | 12.23 |
| MICROCRYSTALLINE AX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| D&C RED NO. 7 CALCIUM LAKE | 3.61 |
| TITANIUM DIOXIDE COATED MICA (1) | 19.95 |
| Example 28 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| D&C RED NO. 6 BARIUM LAKE | 3.61 |
| TITANIUM DIOXIDE COATED MICA (1) | 19.95 |
| Example 29 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| F, D&C YELLOW NO. 5 ALUMINIUM LAKE | 18.66 |
| TITANIUM DIOXIDE COATED MICA (2) | 4.90 |
| Example 30 | |
| CARNAUBA | 3.63 |
| OZOKERITE | 12.23 |
| MICROCRYSTALLINE WAX | 6.18 |
| LANOLIN | 6.82 |

|  | % W/W |
| --- | --- |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| IRON OXIDES (4) | 18.66 |
| TITANIUM DIOXIDE COATED MICA (2) | 4.90 |
| Example 31 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| D&C RED NO. 7 CALCIUM LAKE | 18.66 |
| TITANIUM DIOXIDE COATED MICA (2) | 4.90 |
| Example 32 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| D&C RED NO. 6 BARIUM LAKE | 18.66 |
| TITANIUM DIOXIDE COATED MICA (2) | 4.90 |
| Example 33 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| TITANIUM DIOXIDE | 18.66 |
| TITANIUM DIOXIDE COATED MICA (2) | 4.90 |
| Example 34 | |
| CARNAUBA | 3.63 |
| OZOKERITE | 12.23 |
| MICROCRYSTALLINE WAX | 6.18 |
| LANOLIN | 6.82 |
| OLEYL ALCOHOL | 13.44 |
| CASTOR OIL | 34.01 |
| BUTYLATED HYDROXYANISOLE | 0.03 |
| PROPYL-P-HYDROXYBENZOATE | 0.10 |
| TITANIUM DIOXIDE COATED MICA (1) | 23.56 |
| OIL BLEND 2 | |
| CASTOR OIL | 68.29 |
| LANOLIN OIL | 15.91 |
| OLEYL ALCOHOL | 13.30 |
| SWEET ALMOND OIL | 2.37 |
| PROPYL-P-HYDROXYBENZOATE | 0.10 |
| BUTYLATED HYDROXYANISOLE | 0.03 |

The lipsticks given in Examples 35–40 are prepared in an analogous manner to Examples 15–20 in Range 1.

Examples of formulae for lipsticks

Example 35 (Fuchsia/Arethyst) Shade 1

10 of Example 31, 2 of Example 22 and 4 Doses Oil end 2.

Example 36 (Claret/Mulberry) Shade 41

8 of Example 32, 4 of Example 22 and 4 Doses Oil end 2.

Example 37 (Ruby/Pink) Shade 81

4 of Example 33, 2 of Example 31, 6 of Example 32 and Doses Oil Blend 2.

Example 38 (Almond/Spice) Shade 121

6 of Example 22, 4 of Example 32, 2 of Example 30 and 4 Doses Oil Blend 2.

Example 39 (Russet/Sienna) Shade 161

2 of Example 22, 2 of Example 33, 6 of Example 32, 2 of Example 30 and 4 Doses Oil Blend 2.

Example 40 (Flame/Coral) Shade 201

10 of Example 22, 2 of Example 33 and 4 Doses Oil Blend 2.

We claim:

1. A process for the manufacture of a lipstick comprising the steps of melting a combination of color pellets with a measured amount of an oil blend to form a melted product;

mixing the melted product to form a homogeneous lipstick base composition; and moulding said base composition into a lipstick of a predetermined color; wherein each color pellet comprises a) 1–50% by weight of a wax component comprising as least one cosmetically acceptable wax selected from the group consisting of a plant wax, a vegetable wax, a paraffin wax, an animal wax, and a synthetic wax.

b) 30–65% by weight of an oil component selected from the group consisting of at least one cosmetically acceptable oil and at least one cosmetically acceptable fat, said cosmetically acceptable oil being selected from the group consisting of a natural oil, a synthetic ester, a fatty oil and a fatty alcohol, and said cosmetically acceptable fat being selected from the group consisting of an animal fat, a vegetable fat and a mineral fat, and c) 10–35% by weight of at feast one member selected from the group consisting of a pigment and a pearlising agent; and wherein the oil blend comprises a mixture of more than one cosmetically acceptable oils selected from the group consisting of natural oils, synthetic esters, fatty oils and fatty alcohols and wherein the lipstick further comprises at least one ingredient selected from the group consisting of gloss modifiers texture modifiers, moisturizing agents, soothing agents, conditioners, vitamins, sunscreens, preservatives, and antioxidants.

2. A process as claimed in claim 1, wherein the cosmetically acceptable wax is selected from the group consisting of carnauba wax, candelilla wax, ozokerite, beeswax, lanolin, and hydrogenated castor oil.

3. A process as claimed in claim 1, wherein the cosmetically acceptable oil is selected from the group consisting of castor oil, lanolin oil, almond oil, wheat germ oil, pentaerythritol tetracaprylate, pentaerythritol tetracaprate, triglyceride esters, oleyl alcohol, and octyldodecanol.

4. A process as claimed in claim 1, wherein the cosmetically acceptable fat is selected from the group consisting of wool fat, triglyceride esters, and white soft paraffin.

5. A process as claimed in claim 1, wherein the pigment is selected from the group consisting of an iron oxide, titanium dioxide, a lake, an ultramarine, and an organic dye.

6. A process as claimed in claim 1, wherein the pearlising agent is selected from the group consisting of titanium dioxide coated mica, pigmented mica, pigmented titanium dioxide coated mica, and bismuth oxychloride.

7. A process as claimed in claim 1, wherein the oil blend comprises a mixture of components selected from the group consisting of castor oil, lanolin oil, almond oil, wheat-germ oil, pentaerythritol tetracaprylate, pentaerythritol tetracaprate, triglyceride esters, oleyl alcohol, and octyldodecanol.

8. A process as claimed in claim 1, wherein melting is carried out at a temperature of 40°–120° C.

9. A process as claimed in claim 1, wherein the oil blend further comprises a cosmetically acceptable fat selected from the group consisting of an animal fat, a vegetable fat, and a mineral fat.

10. A process for the manufacture of a lipstick comprising the steps of melting a combination of color pellets with a measured amount of an oil blend to form a melted product;

mixing the melted product to form a homogeneous lipstick base composition; and moulding said base composition into a lipstick of a predetermined color;

wherein each color pellet consists essentially of a) 1–50% by weight of a wax component comprising as least one cosmetically acceptable wax selected from the group consisting of a plant wax, a vegetable wax, a paraffin wax, an animal wax, and a synthetic wax, b) 30–65% by weight of an oil component selected from the group consisting of at least one cosmetically acceptable oil and at least one cosmetically acceptable fat, said cosmetically acceptable oil being selected from the group consisting of a natural oil, a synthetic ester, a fatty oil and a fatty alcohol, and said cosmetically acceptable fat being selected from the group consisting of an animal fat, a vegetable fat and a mineral fat.

c) 10–35% by weight of at least one member selected from the group consisting of a pigment and a pearlising agent, and d) at least one ingredient selected from the group consisting of gloss modifiers texture modifiers, moisturizing agents, soothing agents, conditioners, vitamins, sunscreens, preservatives, and antioxidants; and wherein the oil blend comprises a mixture of more than one cosmetically acceptable oils selected from the group consisting of natural oils, synthetic esters selected from the group consisting of pentaerythritol tetracaprylate and pentaerythritol tetracaprate, fatty oils and fatty alcohols.

* * * * *